(12) United States Patent
Aston et al.

(10) Patent No.: US 9,940,741 B2
(45) Date of Patent: Apr. 10, 2018

(54) DELAY COORDINATE ANALYSIS OF PERIODIC DATA

(71) Applicants: University of Surrey, Surrey (GB); King's College London, London (GB)

(72) Inventors: Philip Aston, Surrey (GB); Mark Christie, London (GB); Manasi Nandi, London (GB)

(73) Assignees: University of Surrey, Surrey (GB); King's College London, London (GB)

(*) Notice: Subject to any disclaimer, the term of this patent is extended or adjusted under 35 U.S.C. 154(b) by 47 days.

(21) Appl. No.: 15/118,405

(22) PCT Filed: Feb. 16, 2015

(86) PCT No.: PCT/GB2015/050429
§ 371 (c)(1),
(2) Date: Aug. 11, 2016

(87) PCT Pub. No.: WO2015/121679
PCT Pub. Date: Aug. 20, 2015

(65) Prior Publication Data
US 2017/0132816 A1  May 11, 2017

(51) Int. Cl.
| | | |
|---|---|---|
| *G06T 11/20* | (2006.01) |
| *A61B 5/00* | (2006.01) |
| *A61B 5/04* | (2006.01) |
| *A61B 5/021* | (2006.01) |

(52) U.S. Cl.
CPC ............ *G06T 11/206* (2013.01); *A61B 5/021* (2013.01); *A61B 5/04012* (2013.01); *A61B 5/412* (2013.01); *A61B 5/7253* (2013.01); *A61B 5/7445* (2013.01)

(58) Field of Classification Search
CPC ..... G06T 11/206; A61B 5/7253; A61B 5/021; A61B 5/412; A61B 5/7445; A61B 5/04012
See application file for complete search history.

(56) References Cited

FOREIGN PATENT DOCUMENTS

| | | |
|---|---|---|
| JP | H0628335 A | 2/1994 |
| WO | WO 2004/086967 A1 | 10/2004 |
| WO | WO 2015/121679 A1 | 8/2015 |

OTHER PUBLICATIONS

Barnard et al., Embedding of Multidimensional Time-Dependent Observations, Physical Review E, vol. 64, No. 4, p. 046201, dated Sep. 4, 2001.
Christie et al., Mathematical Modelling of Heart Rate Changes in the Mouse, pp. 1-16, dated Mar. 4, 2014.
(Continued)

*Primary Examiner* — Maurice L McDowell, Jr.
(74) *Attorney, Agent, or Firm* — Knobbe, Martens, Olson & Bear, LLP

(57) ABSTRACT

Periodic data is analyzed by obtaining a vector of delay coordinates for each one of a plurality of samples of the periodic data in a time window, and transforming each of the vectors into a coordinate system comprising a plurality of predefined vectors, to obtain a projection of an attractor of the periodic data along one of the predefined vectors. The periodic data may be physiological data. Information representing one or more characteristics of the obtained attractor, which is of diagnostic value, is then displayed to enable a diagnosis.

20 Claims, 9 Drawing Sheets

(56) References Cited

OTHER PUBLICATIONS

Fojt O et al., Applying Nonlinear Dynamics to ECG Signal Processing, IEEE Engineering in Medicine and Biology Magazine, IEEE Service Center, Pisacataway, NJ, US, vol. 17, No. 2, pp. 96-101, dated Mar. 2, 1998.

Groth, Visualization of coupling in time series by order recurrence plots, Physical Review E, vol. 72, No. 4, pp. 046220.1-046220.8, dated Oct. 4, 2005.

Nichols et al., Attractor Reconstruction for Non-Linear Systems: A Methodological Note, Mathematical Biosciences, vol. 171, No. 1, pp. 21-32, dated May 1, 2001.

Philip et al., Comparison of Attractor Reconstruction and HRV Methods for Analysing Blood Pressure Data, Computing in Cardiology 2013, pades 437-440, dated Sep. 7, 2014.

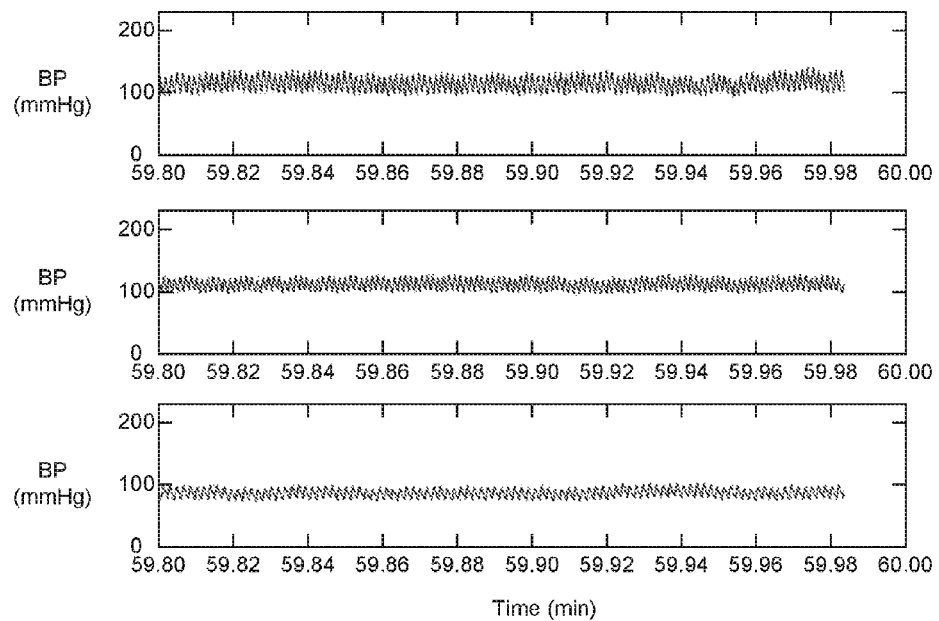
FIG. 8
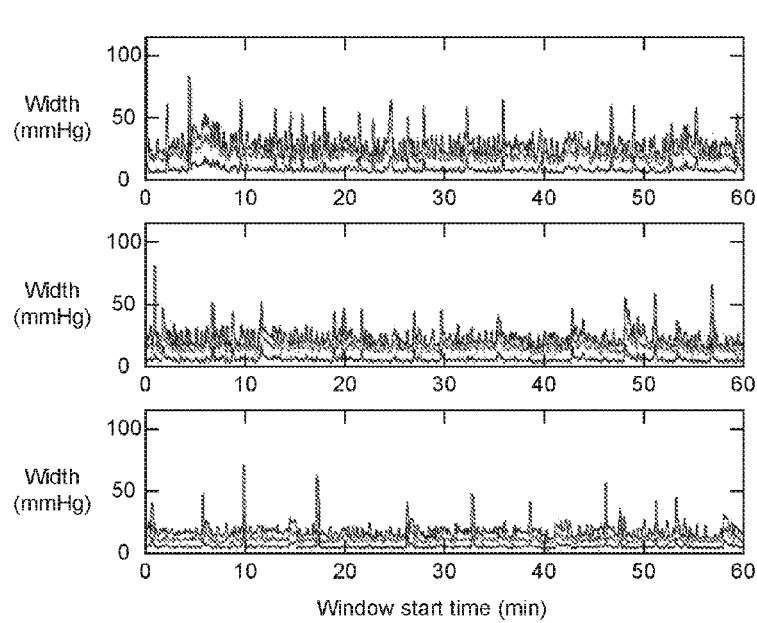 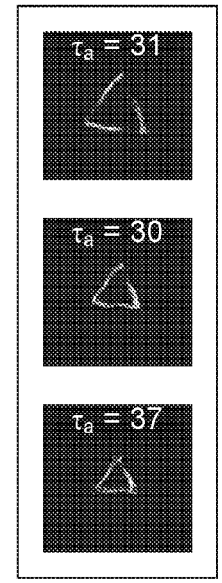
FIG. 9  FIG. 10

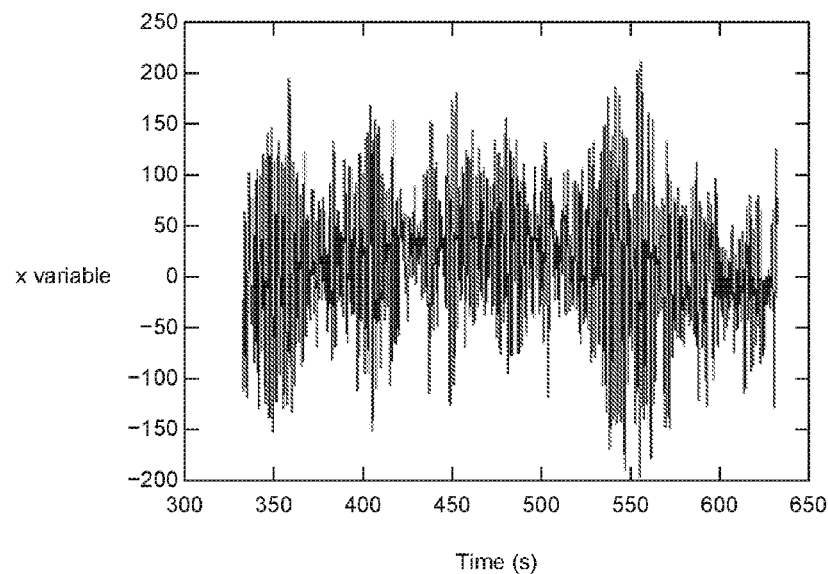
FIG. 17
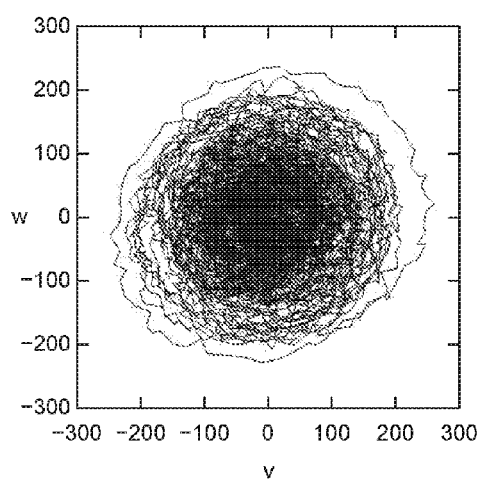 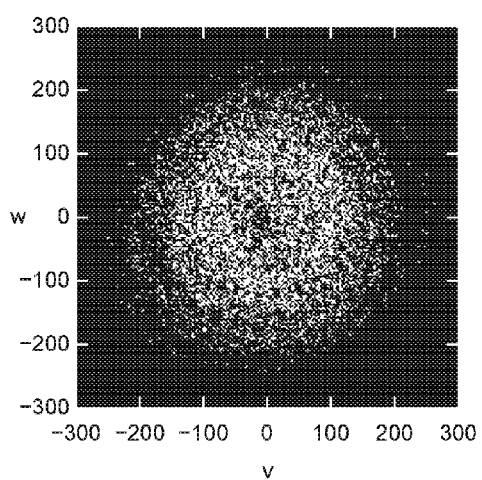
FIG. 18  FIG. 19

DELAY COORDINATE ANALYSIS OF PERIODIC DATA

TECHNICAL FIELD

The present invention relates to analysing periodic data. More particularly, the present invention relates to analysing periodic data by using delay coordinate vectors to reconstruct an attractor derived from the periodic data.

BACKGROUND OF THE INVENTION

The health of an individual can be monitored using various physiological parameters. For example, in a clinical environment a physician may diagnose a particular condition based on increases or decreases in blood pressure over an extended time period. Various analytical methods have been proposed for extracting information of diagnostic value from blood pressure (BP) signals. A conventional approach for obtaining blood pressure readings for long time periods is to record the blood pressure for a 5-minute period, for example at 1-hour intervals, and assume that the blood pressure data collected during this period is representative of the blood pressure throughout the remainder of a longer time interval, during which data was not collected.

Conventional mathematical methods for analysis of a cardiovascular signal such as BP, Electrocardiography (ECG), photoplethysmography (PPG) etc. generally focus on an analysis of the beat-to-beat intervals, expressed as the heart rate variability (HRV). This time series of interval lengths may be analysed using a variety of measures in the time domain. Alternatively, the time series can be analysed in the frequency-domain (Fourier transformed power spectral density; PSD). With a long time window, the results are affected by the non-stationarity of the signal or with a short window, where the signal is more stationary, the frequency resolution is poor. Other methods derive from properties of a chaotic system such as Poincare plots, the largest Lyapunov exponent, entropy, correlation dimension, etc. While these conventional methods are able to provide some diagnostic information from the signal, the biggest drawback is that the majority of the data, namely the shape of the waveform between the intervals, is disregarded. It is known that various conditions affect the shape of the waveform, and clearly HRV ignores such changes.

Instead of using mathematical analysis of the signal to extract information, an alternative approach is to simply display the blood pressure trace, which can be viewed by a physician in order to support a diagnosis. However, information is lost when the blood pressure data is displayed for a relatively long time period, such as 1 hour or more, since display constraints mean that the data is necessarily compressed along the time axis. In blood pressure traces spanning long time periods, it is generally only possible to discern the vertical movement in the signal, and information about both the beat-to-beat shape of the waveform and the majority of the frequency-domain is lost.

The invention is made in this context.

SUMMARY OF THE INVENTION

According to a first aspect of the invention, there is provided a method of analysing periodic data, the method comprising: obtaining a vector of delay coordinates for each one of a plurality of samples of the periodic data in a time window; transforming each of the vectors into a coordinate system comprising a plurality of predefined vectors, to obtain a projection of an attractor of the periodic data along one of the predefined vectors; and displaying information representing one or more characteristics of the obtained attractor. The periodic data may be physiological data or may be another type of data, for example engineering data. It should be understood that 'periodic' does not mean that a signal represented by the data is perfectly periodic. Periodic data may also be referred to as 'pseudo-periodic' or 'approximately periodic' data.

The method can further comprise: determining a repeat period T of a periodic waveform in the periodic data; and selecting a value for a time delay $\tau$ based on the determined repeat period, wherein the vectors of delay coordinates are obtained based on the selected value of the time delay $\tau$. The information representing characteristics of the attractor can include the repeat period T and/or measures derived from T. For example, when analysing periodic physiological data relating to heart rate of a subject, such as blood pressure data or ECG data, displaying information representing characteristics of the attractor can include displaying the heart rate and/or heart rate variability.

The information representing one or more characteristics of the obtained attractor can include a visual representation of the attractor projected along said predefined vector.

The information representing one or more characteristics of the obtained attractor can include the value of a predefined quantity relating to the attractor.

The method can further comprise: determining a function relating to one or more of a density, shape, orientation, symmetry and size of the attractor projected along said predefined vector; and determining the value of the predefined quantity from the function.

The method can further comprise: obtaining a plurality of attractors by moving the time window through the periodic data; and determining a new function relating to one or more of the density, shape, orientation, symmetry and size of the attractor and a new value of the predefined quantity for each of the obtained attractors, wherein displaying the information representing one or more characteristics of the attractor can comprise displaying an animation of the attractors and/or the functions, and/or can comprise plotting a time trace of the predefined quantity against time.

The method can further comprise: searching for one or more peaks in the time trace of the predefined quantity; and in response to one or more peaks being found, displaying information relating to the one or more peaks.

The predefined quantity can relate to a width, density, shape, or size of a band in the projection of the attractor along said predefined vector, or can relate to the orientation, symmetry or size of the attractor in the projection of the attractor along said predefined vector.

The method can further comprise searching for an irregular event in the periodic data, based on the predefined quantity relating to the width of the band in the projection of the attractor along said predefined vector.

The obtained vectors of delay coordinates are three-dimensional vectors [x, y, z], and said predefined vector is parallel to the axis x=y=z.

According to a second aspect of the invention, there is provided a non-transitory computer-readable storage medium arranged to store software instructions which, when executed on one or more processors, perform the method.

The periodic data can be physiological data, and the method can preferably comprise diagnosing disease or deviation from baseline in a subject suspected of suffering from disease based on the information representing one or more characteristics of the obtained attractor.

Preferably, the disease being diagnosed is sepsis, shock or a sepsis/shock-related disease, a disease associated with an abnormal rhythm of the heart, or a disease associated with a disorder of the contractility of the heart or disorder of the vascular network.

Hence, in a third aspect, there is provided a method for diagnosing disease or deviation from baseline in a subject, the method comprising: obtaining a vector of delay coordinates for each one of a plurality of samples of the physiological data in a time window; transforming each of the vectors into a coordinate system comprising a plurality of predefined vectors, to obtain a projection of an attractor of the physiological data along one of the predefined vectors; and displaying information representing one or more characteristics of the obtained attractor, wherein a change in said one or more characteristics of the attractor, relative to the corresponding parameter for a subject not suffering from a disease, indicates that the subject is suffering from a disease or deviating from their baseline. The change in one or more characteristics of the attractor can include a change in dimensions of the attractor, a change in a function of the attractor, such as a density, shape, orientation, symmetry or size function, and/or the appearance of peaks in a time trace of a quantity derived from the attractor.

Preferably, the disease being diagnosed is sepsis, shock or a sepsis/shock-related disease, a disease associated with an abnormal rhythm of the heart, or a disease associated with a disorder of the contractility of the heart or disorder of the vascular network.

The subject may be a vertebrate, mammal or domestic animal. Hence, the method may be used on livestock, pets or for other veterinary applications. Most preferably, however, the subject is a human being.

The method may comprise administering, to the subject, a therapeutic agent/intervention for treating the disease, preferably sepsis, shock or a sepsis/shock-related disease. For example, the therapeutic agent may comprise an antimicrobial agent, the use of intravenous fluids, a vasopressor, cardiac ionotrope, or a steroid (e.g corticosteroid). In the case of a disease associated with an abnormal rhythm of the heart, an anti-arrhythmic drug may be administered, or an intervention carried out to restore the normal electrical rhythm of the heart. In the case of a disorder of the contractility of the heart, a cardiac ionotrope, afterload-reducing or diuretic agent may be administered.

Thus, in a fourth aspect, there is provided a method of treating, ameliorating or preventing sepsis/shock or a sepsis/shock-related disease, a disease associated with an abnormal rhythm of the heart or a disease associated with a disorder of the contractility of the heart or vascular network, the method comprising carrying out the method of the third aspect for diagnosing the disease or deviation from baseline in a test subject, and administering, to the subject, a therapeutic agent or intervention.

The skilled person will appreciate various therapeutic agents which may be administered to the subject once sepsis/shock or a sepsis/shock-related disease has been detected, or is suspected. For example, the therapeutic agent may comprise an antimicrobial agent, the use of intravenous fluids, a vasopressor, cardiac ionotrope, or a steroid (e.g. corticosteroid). In the case of a disease associated with an abnormal rhythm of the heart, an anti-arrhythmic drug may be administered, or an intervention carried out to restore the normal electrical rhythm of the heart. In the case of a disorder of the contractility of the heart, a cardiac ionotrope, afterload-reducing or diuretic agent may be administered.

According to a fifth aspect of the invention, there is provided apparatus for analysing periodic data, the apparatus comprising: a delay coordinate unit configured to obtain a vector of delay coordinates for each one of a plurality of samples of the periodic data in a time window; a transforming unit configured to transform each of the vectors into a coordinate system comprising a plurality of predefined vectors, to obtain a projection of an attractor of the periodic data along one of the predefined vectors; and a display controller configured to display information representing one or more characteristics of the obtained attractor on a display.

The apparatus can further comprise a time delay setting unit configured to determine a repeat period T of a periodic waveform in the periodic data, and select a value for a time delay $\tau$ based on the determined repeat period, wherein the delay coordinate unit can be configured to obtain the vectors of delay coordinates based on the value of the time delay $\tau$ selected by the time delay setting unit. The repeat period T, and/or measures derived from T, such as heart rate and heart rate variability may also be displayed.

The information representing one or more characteristics of the obtained attractor can include a visual representation of the attractor projected along the predefined vector.

The information representing one or more characteristics of the obtained attractor can include the value of a predefined quantity relating to the attractor.

The apparatus can further comprise: a function generating unit configured to determine a function relating to one or more of a density, shape, orientation, symmetry and size of the attractor projected along said predefined vector, and determine the value of the predefined quantity from the function.

The delay coordinate unit and the transforming unit can be further configured to obtain a plurality of attractors by moving the time window through the periodic data, the function generating unit can be further configured to determine a new function and a new value of the predefined quantity for each of the obtained attractors, and the display controller can be configured to display the information representing one or more characteristics of the attractor by displaying an animation of the attractors and/or the function, and/or by plotting a time trace of the predefined quantity against time.

The apparatus can further comprise: a peak detector configured to search for one or more peaks in the time trace of the predefined quantity, wherein in response to one or more peaks being found, the display controller is configured to display information relating to the one or more peaks.

The predefined quantity can relate to a width of a band in the projection of the attractor along said predefined vector.

The apparatus can further comprise: a searching unit configured to search for an irregular event in the periodic data, based on the predefined quantity relating to the width, density, shape, or size of the band, or the orientation, symmetry or size of the attractor, in the projection of the attractor along said predefined vector.

The obtained vectors of delay coordinates can be three-dimensional vectors [x, y, z], and said predefined vector can be parallel to the axis x=y=z.

BRIEF DESCRIPTION OF THE DRAWINGS

Embodiments of the present invention will now be described, by way of example only, with reference to the accompanying drawings, in which:

FIG. 8 illustrates blood pressure traces recorded from a mouse at different times after induction of septic shock, according to an embodiment of the present invention;

FIG. 9 illustrates time-varying measures derived from attractors for the blood pressure data of FIG. 8, according to an embodiment of the present invention;

FIG. 10 illustrates the attractors from which the parameters plotted in FIG. 9 are derived, according to an embodiment of the present invention;

FIG. 17 illustrates bending moment data from a wind turbine, according to an embodiment of the present invention;

FIG. 18 illustrates an attractor derived from the bending moment data shown in FIG. 17, according to an embodiment of the present invention;

FIG. 19 is a density plot for the attractor shown in FIG. 18, according to an embodiment of the present invention;

DETAILED DESCRIPTION

Embodiments of the present invention can be used to analyse periodic data and display information representing one or more characteristics of an attractor of the periodic data, which can be of diagnostic value.

The periodic data may relate to a periodic physiological signal, that is, a signal comprising a repeating waveform. However, in some embodiments of the invention the periodic signal being analysed is not perfectly periodic. It should be understood that 'periodic' in this context does not mean that a signal represented by the data is perfectly periodic, and the observed periodicity can vary slightly from one repeat period to the next, and may vary significantly over longer time periods. This is particularly true of physiological signals, but also applies to any type of pseudo-periodic or approximately periodic data in other contexts, for example in engineering applications. Similar, any references herein to a 'repeating waveform' in the periodic data should be understood as meaning a waveform that is similar, but not necessarily identical, from one repeat period to the next. References to a repeat period T should also be understood as meaning an average of the cycle lengths in the periodic data.

Figure 1:
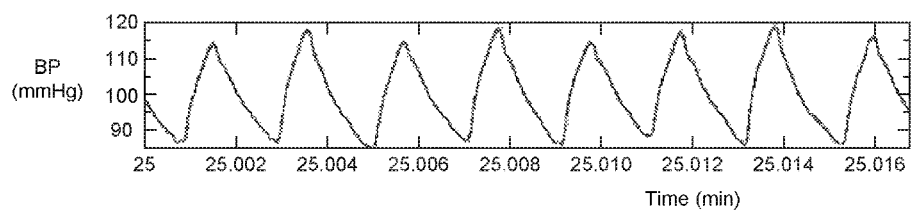
FIG. 1 illustrates a blood pressure trace, according to an embodiment of the present invention.
Figure 11A:
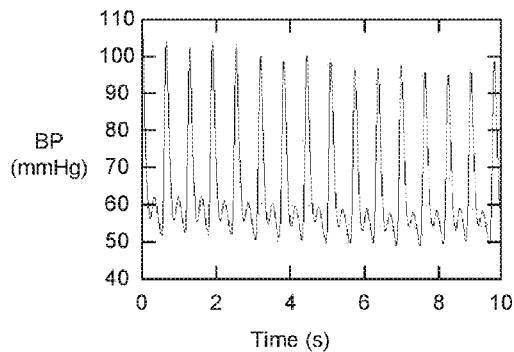
FIGS. 11A to 11F illustrate the attractors derived from a) human arterial BP, b) human pulse oximetry, c) human central venous pressure, d) human ECG, e) human intracranial pressure and f) human respiration signals, according to an embodiment of the present invention.
Figure 11A:
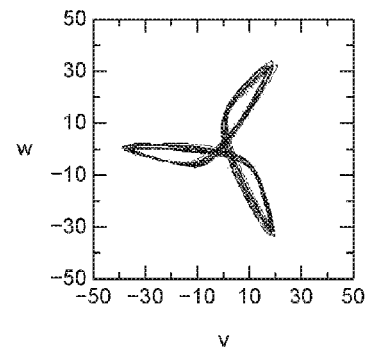
Figure 11B:
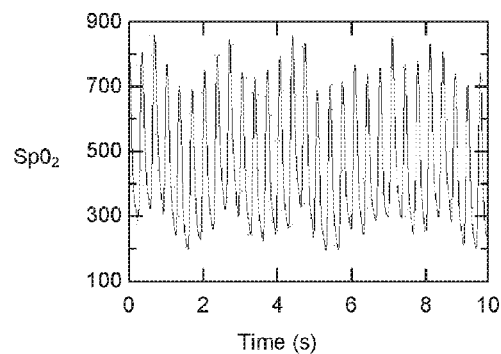
Figure 11B:
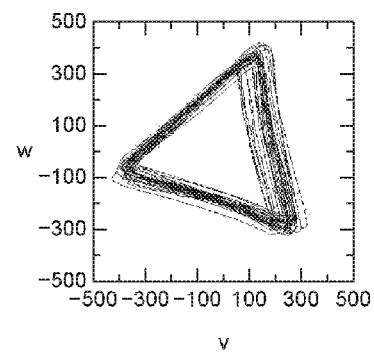
Figure 11C:
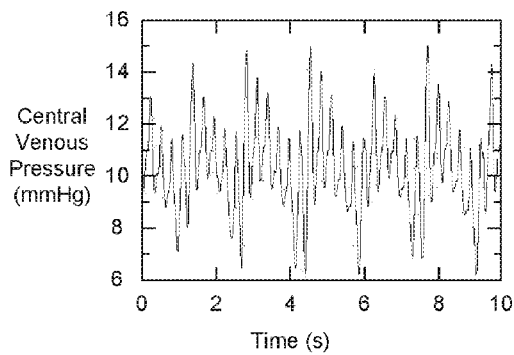
Figure 11C:
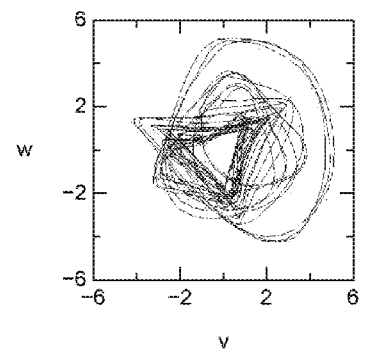
Figure 11D:
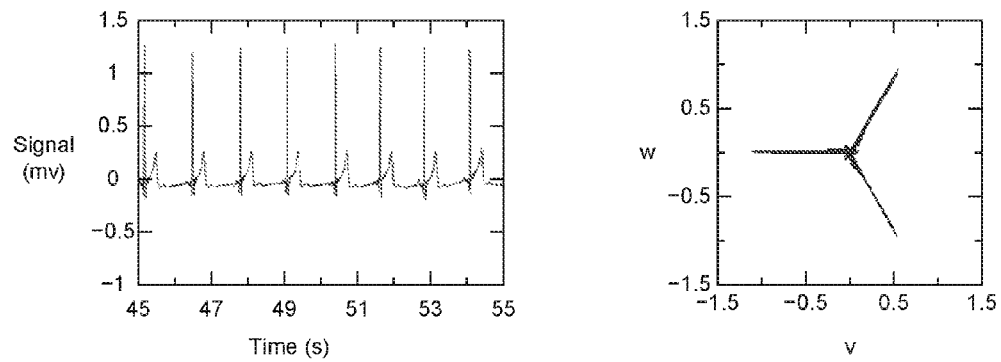
Figure 11E:
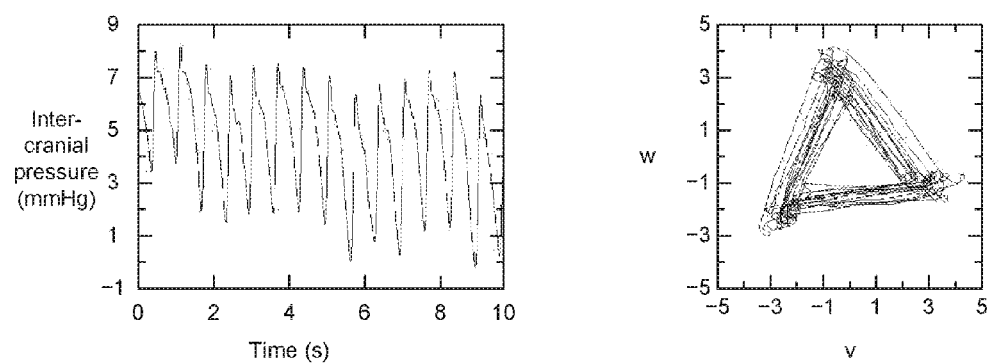
Figure 11F:
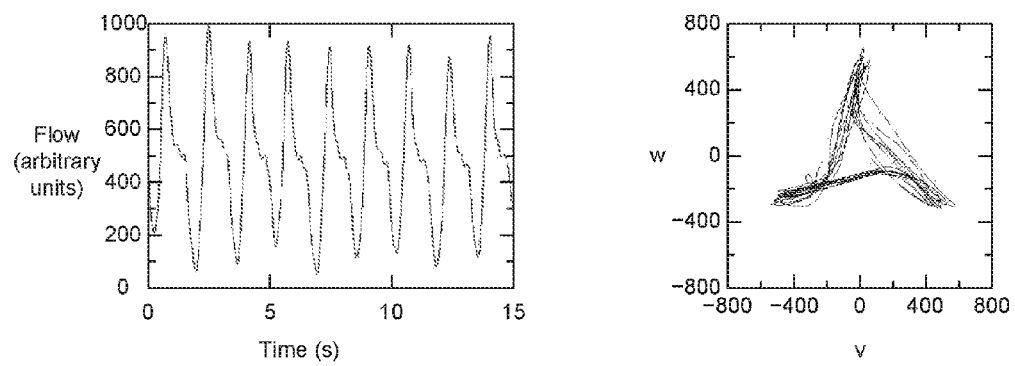

An example of physiological data which can be analysed in an embodiment of the invention is shown in FIG. 1, which illustrates a blood pressure signal, and in FIGS. 11A to 11F. In each of FIGS. 11A to 11F, the left-hand figure illustrates the raw physiological data, and the right-hand figure illustrates an attractor derived from the physiological data. FIG. 11A illustrates human arterial BP data, FIG. 11B illustrates human pulse oximetry data, FIG. 11C illustrates human central venous pressure data, FIG. 11D illustrates human ECG data, FIG. 11E illustrates human intracranial pressure data, and FIG. 10 illustrates human respiration data. However, in other embodiments of the invention different types of signals can be analysed, including but not limited to Left Ventricular Pressure (LVP), Electroencephalography (EEG), Electromyography (EMG), PPG, Doppler blood flow, accelerometry (tremor), gait monitoring, continuous blood glucose, and acoustic (speech) signals.

Figure 2:
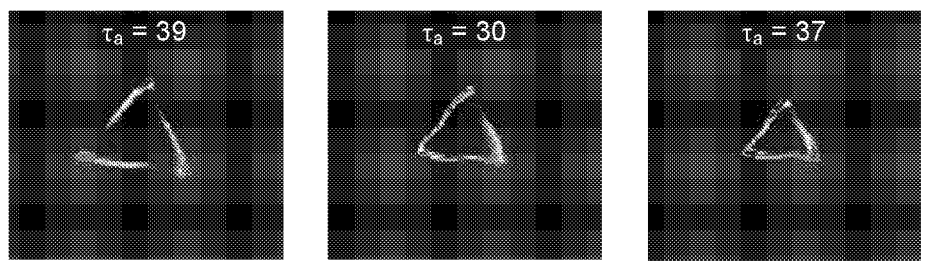
FIG. 2 illustrates attractors for three sets of blood pressure data, according to an embodiment of the present invention.

The diagnostic value of information relating to the attractor is shown in FIG. 2, which illustrates attractors for three sets of blood pressure signals from a single conscious animal. Investigations by the inventors have revealed that the attractor provides information of diagnostic relevance which is not directly accessible from a simple blood pressure trace such as the one shown in FIG. 1. In the example shown in FIG. 2, the attractor on the left is constructed from blood pressure data for a healthy subject, whereas the attractors on the middle and right are constructed from blood pressure data for a subject in early and latter stages of septic shock, respectively. Although both attractors are approximately triangular, it can be seen that under septic shock the attractor shrinks and rotates with respect to the attractor for the healthy subject, providing additional information that cannot be visualised by inspection of the blood pressure trace alone (FIG. 8 upper two panels). Examples of relevant characteristics of the attractor for diagnostic purposes include the attractor shape, orientation, symmetry, density, and size.

Figures 6, 7:
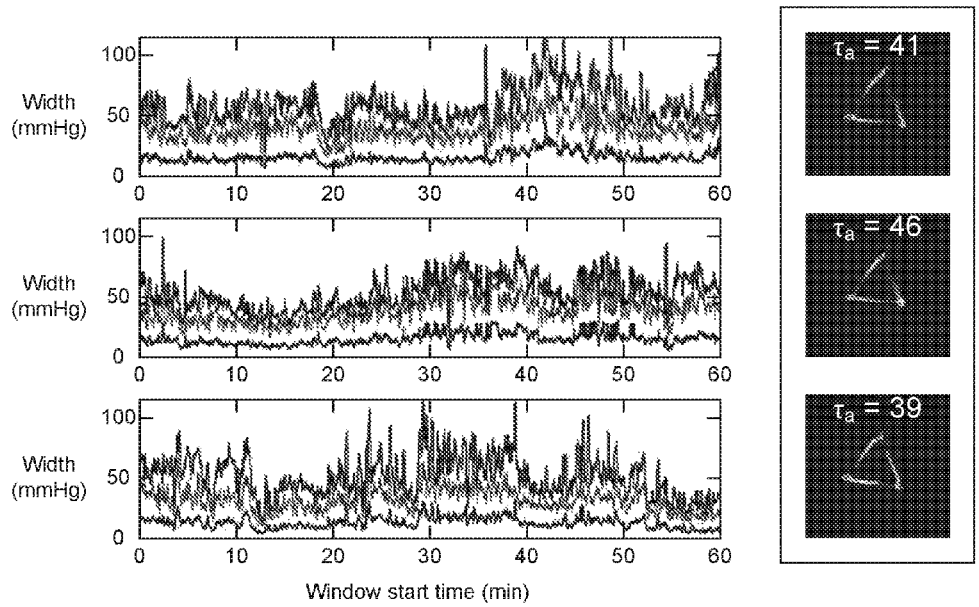
FIG. 6 illustrates time-varying maximum, threshold maximum and standard deviation measures relating to a one-dimensional density function derived from an attractor, for the blood pressure data of FIG. 5, according to an embodiment of the present invention.
FIG. 7 illustrates the attractors from which the parameters plotted in FIG. 6 are derived, according to an embodiment of the present invention.

As described above, information representing one or more characteristics of the attractor is displayed in order to enable a diagnosis. In some embodiments, the displayed information is a direct visual representation of the attractor, as shown in FIG. 2. In other embodiments, the displayed information can be one or more predefined quantities derived from the attractor. For example, a predefined quantity can be displayed as a time trace, as shown in FIG. 6. Examples of quantities that can be derived will be described in more detail later, and include the mean, standard deviation, maximum and minimum, and threshold maximum and minimum values of a function derived from the attractor. Such quantities can provide information about characteristics such as the shape, orientation, symmetry, density or size of the attractor, and therefore may have diagnostic relevance. In some embodiments, both a visual representation of the attractor and quantitative measures relating to the attractor are displayed. The visual representation of the attractor can be displayed as a static image, or an animation showing evolution of the attractor over time can be displayed by moving a time window through the data, and sequentially displaying the reconstructed attractor for different positions of the time window.

In contrast, if plotted as a blood pressure trace such as the one shown in FIG. 1, the blood pressure data sets represented in FIG. 8—upper two panels would produce qualitatively similar traces that would not enable a diagnosis of sepsis. Current clinical diagnosis of sepsis requires blood sampling to ascertain presence of infection or perturbed blood biochemistry. This data is used in conjunction with blood pressure data to support diagnosis. Conventional diagnosis of sepsis from the blood pressure signal is only apparent once marked changes have occurred in the vertical axis, for example once the mean arterial blood pressure has fallen below 70 mmHg. However, at this stage the blood pressure is about 30-40% lower than the 'healthy/baseline state', the patient has already become refractory, and mortality risk substantially increases. Early diagnosis is therefore essential to allow earlier identification and treatment of high-risk patients. In comparison, embodiments of the present invention use attractor reconstruction to provide a fast, convenient, non-invasive method of diagnosing the onset of sepsis prior to marked changes occurring in the vertical direction.

A method of obtaining the attractors shown in FIG. 2, from blood pressure data such as that illustrated in FIG. 1, will now be described in detail.

The blood pressure trace illustrated in FIG. 1 was obtained by collecting blood pressure data from a healthy, conscious mouse using an implanted radiotelemetry device at a sample rate of 1000 Hertz (Hz) for a 24 hour period, resulting in a series of large datasets. In the present embodiment, blood pressure data is recorded as a digital signal comprising a plurality of samples. Each sample represents the magnitude of the quantity being measured, in this case blood pressure, at a point in time. In other embodiments, samples can be obtained from a received analogue signal. The invention is not limited to use with a sample rate of 1000 Hz, and in other embodiments any suitable sample rate can be used, depending on the typical timescale for the signal type being measured.

In FIG. 1, the blood pressure signal for a time period of 1 second (0.0167 minutes) is illustrated. However, in general, embodiments of the present invention are not limited to a signal duration of 1 second, but can be used to analyse physiological data for any given time period.

As shown in FIG. 1, the blood pressure data shows cyclic behaviour due to the regular heartbeat. The beat-to-beat interval for this data is approximately 120 milliseconds (ms), corresponding to a heart rate of 500 beats per minute, and so there are around 120 data points per cycle. However, the blood pressure signal is not periodic as beat-to-beat variability in both period and waveform shape results in variation in this signal over time. Because the signal is not stationary when viewed over long time periods, conventional Fourier-based techniques are limited to analysing signals of relatively short duration during which the physiological variable being measured is approximately stationary, which results in poor frequency resolution.

Figure 3:
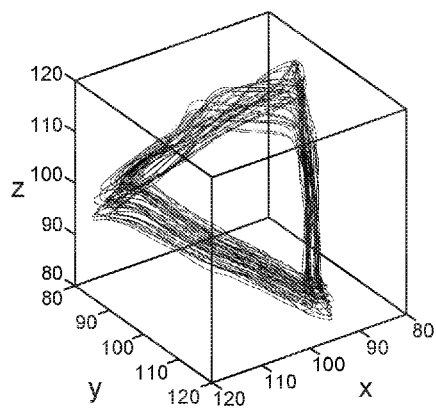
FIG. 3 illustrates a trajectory of a blood pressure signal in three-dimensional reconstructed phase space, according to an embodiment of the present invention.

Referring now to FIG. 3, a trajectory of a blood pressure signal in three-dimensional reconstructed phase space is illustrated, according to an embodiment of the present invention. This trajectory, which can also be referred to as the attractor, is obtained by analysing a blood pressure signal such as the one shown in FIG. 1. Specifically, the trajectory is obtained using a delay coordinate vector method based on Takens' theorem. Takens' theorem allows an attractor to be reconstructed in an n-dimensional 'phase space' for n≥2 from a single signal x(t) by using a vector of delay coordinates as follows:

$$[x(t), x(t-\tau), x(t-2\tau), \ldots, x(t-(n-1)\tau)]$$

where x(t) is the signal value at time t, and $\tau > 0$ is a fixed time delay.

When using Takens' delay coordinates to reconstruct an attractor, it is necessary to choose appropriate values for two key parameters, namely (i) the embedding dimension n, and (ii) the value of the time delay $\tau$.

With regard to the embedding dimension n, Takens showed that an m-dimensional manifold requires 2m+1 delay coordinates for there to be a continuous, injective mapping from the manifold to the reconstructed phase space. However, the dimension of the underlying model or of the attractor of that model is generally not known, particularly in the case of complex physiological signals. Taking the present example of a blood pressure signal, there are many factors that influence the blood pressure in a conscious animal, including the sympathetic nervous system, parasympathetic nervous system, respiratory system and motor activity. Accordingly, a full mathematical model including all possible factors would be highly complex. Even if such a model could be constructed, the dimension of the attractor would still not be known. Thus, a theoretical value for the embedding dimension n is not available. However, there are a variety of methods in the literature for estimating a minimum embedding dimension, for example using a singular value analysis or the method of false nearest neighbours.

In the present embodiment, the value n=3 is chosen for ease of visualisation of the attractor, without attempting to find the optimal embedding dimension. However, in other embodiments different values can be chosen for the embedding dimension n. For example, n=2 could be used in some embodiments, or a value higher than 3 could be chosen. In general, a plurality of embedding dimensions is required (n>1) so that at least one dimension remains after projecting along a predefined axis.

With regard to the time delay $\tau$, if $\tau$ is chosen to be very small then there will be only a small difference between the variables. As a result, the trajectory will always lie close to the axis in the phase space given by $x_1 = x_2 = \ldots = x_n$, where $x_i(t) = x(t-(i-1)\tau)$ for i=1, ..., n. On the other hand, if $\tau$ is chosen to be very large, then there may be little correlation between each of the variables.

Investigations by the inventors have shown that when $\tau$ is equal to ⅓ or ⅔ of the period T of a perfectly periodic signal, the closed loop attractor has $Z_3$ cyclic symmetry when viewed along the axis x=y=z. For physiological data, the value of $\tau$ is chosen to make the density of the projected attractor as close to being $Z_3$ symmetric as possible by minimising a symmetry measure. It can be shown that the optimal time delay is then related to the average cycle length of the signal in the time window. In other embodiments, a fixed value of $\tau$ could be used or a different measure optimised. In the present embodiment, the trajectory shown in FIG. 3 is plotted using a time delay $\tau$ of 45 milliseconds (ms), for 5 seconds of data. Examples of methods that can be used for choosing the time delay $\tau$ in other embodiments of the present invention include a mutual information based method, and a continuity statistic based method. The continuity statistic based method can be used to determine both the optimal time delay and embedding dimension simultaneously.

As described above, the embedding dimension n=3 is used in the present embodiment. Accordingly, two new variables y(t) and z(t) are defined, allowing a three-dimensional vector of delay coordinates to be obtained for each sample of the signal x(t) within a time window as follows:

$$\begin{bmatrix} x(t) \\ y(t) \\ z(t) \end{bmatrix}$$

where $$y(t)=x(t-\tau)$$

$$z(t)=x(t-2\tau)$$

As described above, the trajectory shown in FIG. 3 is obtained by plotting the obtained vectors for data within the defined time window, which in the present example is 5 seconds. In other embodiments, data can be plotted for a time period of longer or shorter duration than 5 seconds.

Although the trajectory plotted in FIG. 3 may appear visually similar to the attractors shown in FIG. 2, an additional processing step is required in order to reconstruct the attractor from the trajectory of FIG. 3. Specifically, a coordinate transformation is applied in order to display a two-dimensional projection of the trajectory along a chosen axis.

Figure 4:
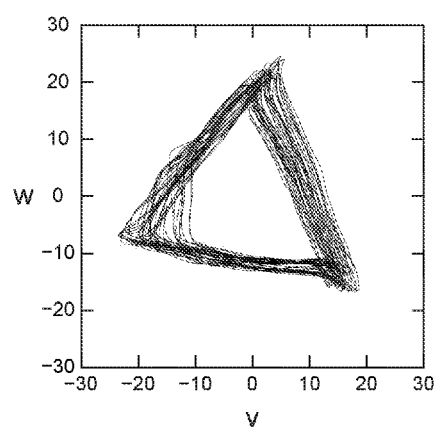
FIG. 4 illustrates a projection of the trajectory of FIG. 3 when viewed along the axis x=y=z, according to an embodiment of the present invention.

Applying a coordinate transformation in this way allows movement of the signal along the chosen axis to be factored out. In the present example of a blood pressure signal, the chosen axis is x=y=z, so that vertical movement of the signal is factored out. The projection of the trace of FIG. 3 onto the plane orthogonal to the x=y=z axis is illustrated in FIG. 4. Since it is the vertical movement that is easily observed in a conventional blood pressure trace, the projection normal to the x=y=z axis contains additional information that is not directly represented in a conventional trace such as the one shown in FIG. 1.

Figure 20:
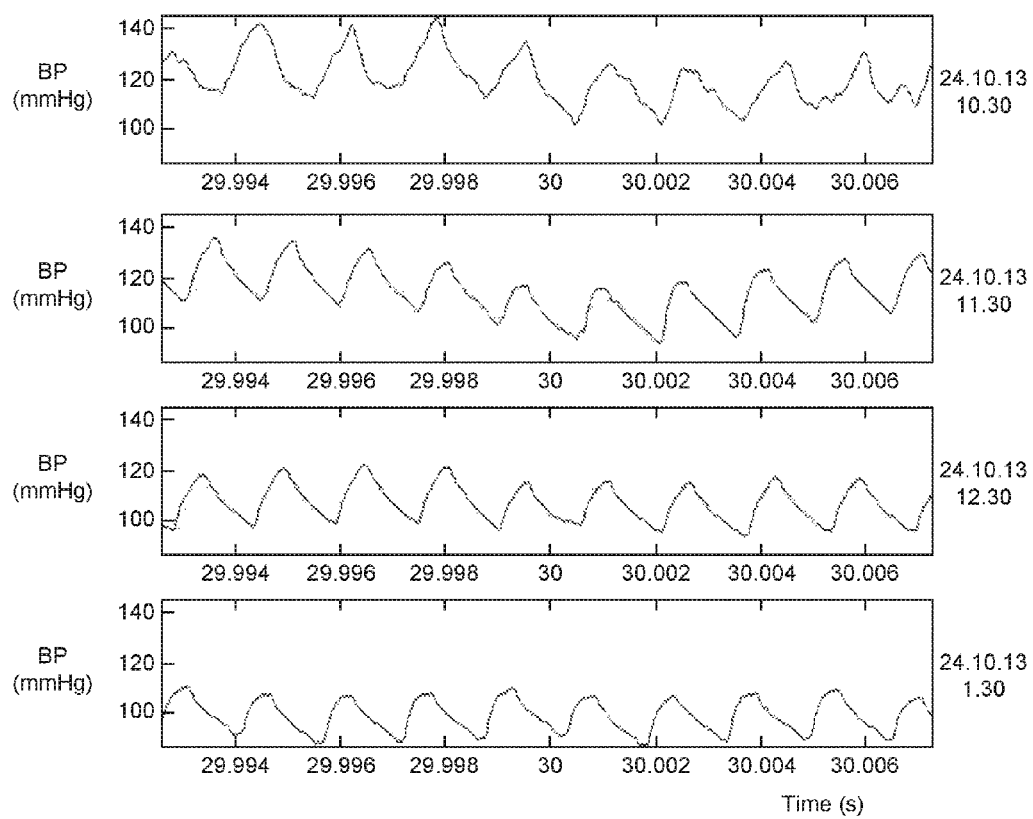
FIG. 20 illustrates blood pressure traces pre-LPS (bacterial lipopolysaccharide) injection (top panel) and post-LPS (bottom three panels)
Figure 21:
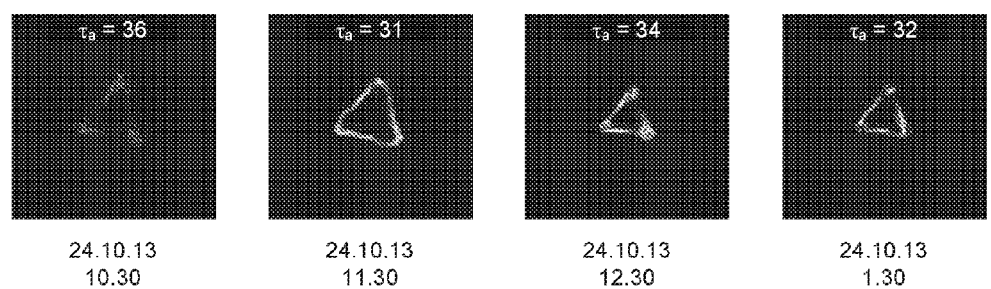
FIG. 21 illustrates attractors derived from the blood pressure traces shown in FIG. 20, according to an embodiment of the present invention.

For example, investigations by the inventors have shown that the orientation of the attractor when viewed in the (v, w) plane depends on the shape of the repeating waveform. Specifically, if each waveform is considered a piecewise linear signal consisting of two linear segments (systole and diastole, respectively) with the break between them occurring at approximately ⅓ of the period, it can be shown that a reduction in the time at which this break point occurs will cause a characteristic increase in the density at the corners of a projected triangular attractor. FIGS. 20 and 21 illustrate the effect of a bacterial lipopolysaccharide (LPS) injection on an attractor derived from blood pressure data, showing the increase in density at the corners of the attractor that occurs post-LPS. FIG. 20 illustrates blood pressure traces pre-LPS (top panel) and post-LPS (bottom three panels), while FIG. 21 illustrates the attractors derived from the pre-LPS blood pressure data and from the post-LPS blood pressure data.

Conversely, an increase in the time at which break point occurs will result in a reduction in the density and rounding of the corners of the attractor derived from blood pressure data. These changes are characteristic of increases and reductions in cardiac contractility, respectively and may be used for the diagnosis of cardiac changes induced by sepsis, shock, cardiotoxic drugs, or pharmacological agents with a therapeutic action on the heart.

Furthermore, a convex downstroke produces a clockwise rotation of the attractor in comparison to a linear downstroke, whereas a concave downstroke produces an anti-clockwise rotation. In blood pressure data, for example, these changes reflect alterations in cardiac afterload, total peripheral resistance and vessel elasticity and may be used for the diagnosis of cardiovascular changes induced by sepsis, vasoactive drugs, or pharmacological agents with a therapeutic action on the cardiovascular system/vascular network. The influence of the shape of the downstroke on the orientation of the attractor can be understood by comparing FIG. 11B, which illustrates an attractor derived from a trace with a convex downstroke, with FIG. 11E, which illustrates an attractor derived from a trace with a concave downstroke.

Investigations by the inventors have also shown that the stability of the 3-fold symmetry of the attractor when viewed in the (v, w) plane depends on the periodicity of the waveform over the time period over which the optimal time delay τ is calculated. It can be shown that brief changes in the periodicity of the waveform will result in large deviations of the attractor orbit for that cycle from the preceding and succeeding cycles, and measurable changes in some of the functions derived from the attractor. These changes reflect changes in cardiac rhythm, or arrhythmias and may be used for the diagnosis of cardiovascular changes caused by atrial fibrillation, ventricular ectopic beats, ischaemic heart disease, disorders of cardiac ion channel function, or pharmacological agents with a cardiotoxic effect on the heart.

Such information about the shape of the waveform is not discernible in a blood pressure trace when viewed over long time periods, as the peak-to-peak distance is compressed.

As described above, when blood pressure data is viewed over relatively long time intervals, for example an hour or more, the individual oscillations can no longer be distinguished. The only information that is readily observable is the vertical motion of the average blood pressure, which will vary depending on whether the individual is resting, moving slowly, active, etc. This natural variation means that the signal is non-stationary, which causes problems when trying to analyse the frequencies in the signal, for example using a conventional Fast Fourier Transform (FFT) based approach. By factoring out the easily observed vertical motion, embodiments of the present invention are able to extract information from the reduced attractor in order to detect other, less obvious, changes that are occurring in the data.

A more detailed explanation is as follows. For a reconstructed attractor in a three-dimensional space, such as the one shown in FIG. 3, if the time delay is chosen to be the trivial case of τ=0 then x=y=z, and so the trajectory in the reconstructed phase space simply moves up and down the line in the phase space defined by x=y=z, which can be referred to as the central axis. For small τ, the trajectory will stay near to this axis, since the three points will be close together, and so the dominant motion will again be up and down this central axis. However, for larger τ, the trajectory will start to move away from this axis. As the blood pressure rises and falls, the motion projected onto the central axis will also rise and fall. Therefore a new coordinate system is defined, consisting of the central axis together with two axes that are orthogonal to this axis, and each other. We then normalise each of these vectors to give an orthonormal basis.

Although in the present embodiment the new coordinate system comprises three orthogonal unit vectors, in other embodiments the new vectors may not be unit vectors, in which case the step of normalising the vectors to give an orthonormal basis can be omitted. Also, in some embodiments the vectors may not be orthogonal, in which case an alternative central axis can be defined other than x=y=z.

In more detail, a unit vector in the direction of the central axis x=y=z is given by $v_1=(1, 1, 1)^T/\sqrt{3}$. In order to project the attractor onto the plane normal to the central axis, the remaining two basis vectors must be orthogonal to this one and to each other and we choose the unit vectors $v_2=(1, 1, -2)^T/\sqrt{6}$ and $v_3=(1,-1, 0)^T/\sqrt{2}$. Any rotation of these two vectors in the plane orthogonal to the central axis is also possible. Thus, the matrix M, which has columns $v_1$, $v_2$ and $v_3$, is an orthogonal matrix. If we have coordinates (u, v, w) with respect to the new basis vectors, then the old and new coordinates are related by:

$$\begin{bmatrix} x \\ y \\ z \end{bmatrix} = uv_1 + vv_2 + wv_3$$

or equivalently $$x=Mu$$

where $x=(x, y, z)^T$ and $u=(u, v, w)^T$. Thus, the new coordinates are defined by $$u=M^T x$$

since M is an orthogonal matrix, or equivalently $$u = v_1^T x = \frac{1}{\sqrt{3}}(x+y+z)$$

$$v = v_2^T x = \frac{1}{\sqrt{6}}(x+y-2z)$$

$$w = v_3^T x = \frac{1}{\sqrt{2}}(x-y)$$

From this, we see that u is almost the mean of the three original variables x, y and z, and in some embodiments u can be redefined to be the mean.

The new variables v and w are the coordinates of a point in the three-dimensional phase space projected onto the plane orthogonal to the line x=y=z. The trajectory shown in FIG. 3 projected onto this plane is shown in FIG. 4. The new variable u(t) captures the vertical motion of the blood pressure signal, which is the information represented in a conventional blood pressure trace. The other two variables v(t) and w(t) are not affected by this motion, and hence provide additional information about the signal that can be of diagnostic value.

Another advantage offered by embodiments of the present invention, in comparison to prior art analytical methods, is that all of the data for a relatively long time period can be analysed and plotted. In contrast, conventional methods focus either on the vertical movement of the signal or on the beat-to-beat variation, and discard the data collected between beats.

As described above, information representing one or more characteristics of the attractor is displayed in order to enable a diagnosis. Depending on the embodiment, the displayed information can include a visual representation of the attractor projected onto the predefined plane, for example the (v, w) plane as shown in FIG. 2, and/or can include one or more predefined quantities derived from the attractor. The information can be displayed in a static manner, for example by simply displaying the attractor for data within a fixed time window and/or displaying the values of one or more predefined quantities derived from the attractor.

However, in some embodiments the information can be displayed in a dynamic manner, by displaying an animation showing the evolution of the attractor over time, and/or by plotting a time trace of the values of one or more of the predefined quantities. Dynamic information can be obtained by moving the time window through the data and constructing attractors for different positions of the time window. For each position of the time window, a new attractor can be constructed, and new values of the predefined quantities can be derived. This approach is used to plot the traces shown in FIGS. 6 and 9, in which the distance along the horizontal axis represents the start time of the window. The different positions of the time window can overlap, that is, can include overlapping data sets, or the different positions can be spaced apart in time and can include separate data sets.

A method of deriving various predefined quantities based on a density function of the attractor will now be described.

A signal that is perfectly periodic will produce a closed trajectory when plotted in phase space. However, as explained above, embodiments of the present invention can be applied to signals that are not perfectly periodic, with the result that the trajectory in phase space is dispersed, as shown in FIGS. 3 and 4. When a long trajectory is plotted in the (v, w) plane the shape and character of the attractor can quickly become obscured. Therefore when analysing data over relatively long time periods, in some embodiments of the present invention a visual representation of the attractor density (e.g. FIGS. 2, 7 and 10) can be displayed instead of a line representation (e.g. FIG. 4), to address this problem.

In the present embodiment, the density function is obtained by reconstructing the attractor as described above, to generate the density in the (v, w) plane. A matrix $D(\tau)$ is then computed which gives the density of the attractor in each box within a grid of boxes over the (v, w) plane. In the present embodiment a grid of 112×112 boxes is used to compute the matrix $D(\tau)$, which hereinafter will be referred to as the density matrix, but in other embodiments different sized grids could be used.

A variety of measures can then be extracted from the density matrix $D(\tau)$. For example, a symmetry measure can be defined which provides an indication of how symmetric the attractor is. Various definitions of the symmetry measure are possible, depending on the desired shape of the attractor. For example, in the present embodiment we find a value of the time delay $\tau$ which gives an attractor that is as close to being $Z_3$ symmetric as possible when projected onto the (v, w) plane. For an ideal periodic signal, this attractor will have this threefold rotational symmetry around the x=y=z axis, and so in the present embodiment we define a matrix $D_S(\tau)$ as:

$$D_S(\tau)=\frac{1}{3}(D_1(\tau)+D_2(\tau)+D_3(\tau))$$

where the first density matrix $D_1(\tau)=D(\tau)$, the second density matrix $D_2(\tau)$ is a density matrix obtained for the data rotated in the (v, w) plane by $2\pi/3$, and the third density matrix $D_3(\tau)$ is a density matrix obtained for the data rotated in the (v, w) plane by $4\pi/3$.

A symmetry measure $S(\tau)$ is then defined as:

$$S(\tau)=\|D(\tau)-D_S(\tau)\|_2$$

In the ideal case of a perfectly repeating waveform with a constant repeat period T, and a time delay τ equal to (⅓)T or (⅔)T, $D_S(τ)$ will be equal to $D(τ)$ and $S(τ)$ will be equal to zero. The symmetry measure can therefore be used to select a suitable value of the time delay τ, by computing $S(τ)$ for different values of τ to find a value of the time delay τ which minimises the function $S(τ)$.

However, in other embodiments this procedure can be omitted, and different methods can be used to select the time delay τ. For example, the mean peak-to-peak distance in the physiological data can be taken as the repeat period T, or the repeat period T can be found using autocorrelation, and the time delay τ can be chosen as ⅓ or ⅔ of this repeat period T. Alternatively, the time delay τ could be fixed or could simply be chosen by trial-and-error.

The density matrix $D(τ)$ can also be used to obtain other scalar measures that provide further information of diagnostic value. For example, the density function can be used to derive information about the thickness of the bands along the sides of the triangular attractor. If the data contains occasional irregular events, this would appear in the attractor as brief excursions away from the triangle. A method of quantifying this is described in detail below.

We begin by considering only the portion of the symmetric density matrix $D_S(τ)$ that contains the side of the attractor parallel to the v axis. The entries in $D_S(τ)$ along the v direction for this side of the attractor are summed to give a new density function d(w) which depends only on values of w. The constant w value along this side of the attractor for a simple piecewise linear periodic signal has been shown to be equal to $-h/(2\sqrt{2})$, where h corresponds to the pulse pressure, that is, the difference in height between the peak and trough in the signal. The density function d(w) therefore provides information about the distribution of pulse pressures in the signal.

From d(w) we can derive a number of scalar measures, including the mean, the standard deviation, the maximum and minimum values. It is also possible to define threshold maximum and minimum values, which are the maximum and minimum values of h between which the density is greater than a specified threshold value.

If the data contains occasional irregular events, this will result in a large difference between the maximum and threshold maximum and/or between the minimum and threshold minimum. Thus, a large difference in these quantities is an indicator of rare irregular events occurring in the data. Alternatively, a large difference between the maximum and the standard deviation could be used to identify an irregular event.

In this way, information relating to the width of the band in the projection of the attractor can be used to search for an irregular event in the physiological data, such as an arrhythmia. This approach is made possible by the fact that the analytical methods used in embodiments of the invention analyse the entire data set within the time window, rather than focussing solely on peak-to-peak variation and discarding intervening data points, for example. This represents a significant improvement over the conventional approach, which involves large quantities of data being reviewed by human operators to identify an irregular event.

An example of how the above-described analytical methods can be used to diagnose the onset of sepsis from blood pressure data will now be described, with reference to FIGS. 5 to 10.

Figure 5:
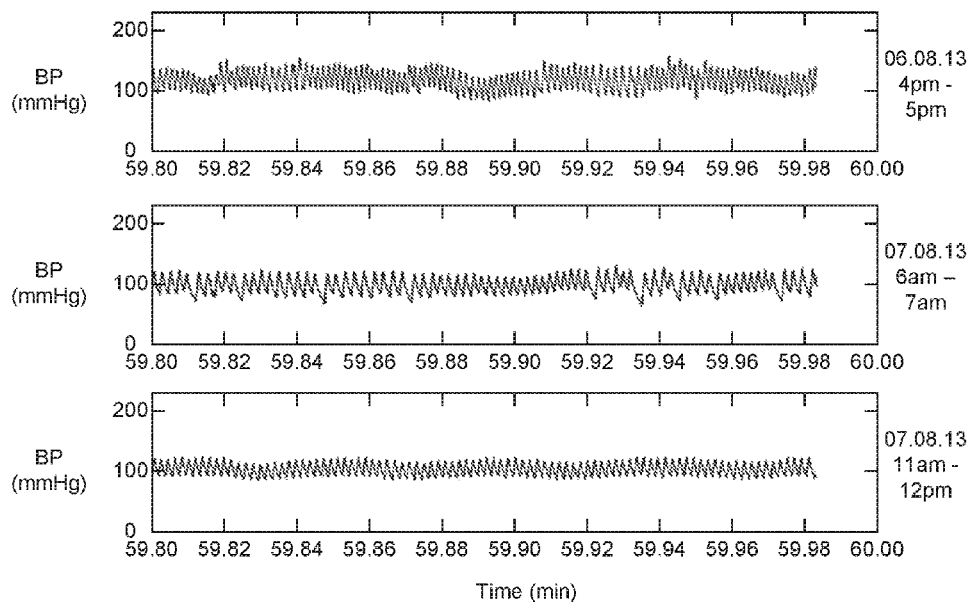
FIG. 5 illustrates blood pressure traces recorded from a healthy mouse at different times of day.

FIG. 5 illustrates traces for blood pressure data collected from a healthy mouse at different times of day, showing different heart rates and different blood pressures values.

FIG. 7 illustrates attractors constructed using the above-described method, corresponding to the blood pressure traces of FIG. 5. It can be seen from FIG. 7 that the attractors are virtually identical even though the pulse rate and blood pressure vary between the blood pressure traces. The attractors illustrated in FIG. 7 are therefore characteristic of a healthy mouse. Similarly, plots of corresponding scalar measures derived from the attractors shown in FIG. 7 are illustrated in FIG. 6, and it can be seen that the parameters remain chaotic for a healthy mouse regardless of changes in the pulse rate or blood pressure. In each of FIGS. 5, 6 and 7, the top panel illustrates data recorded between 4 pm and 5 pm, the middle panel illustrates data recorded between 6 am and 7 am, and the bottom panel illustrates data recorded between 11 am and 12 pm.

In contrast, FIGS. 8, 9 and 10 illustrate corresponding blood pressure traces, scalar measures, and attractors for a mouse at different stages during the onset of LPS induced septic shock. In FIGS. 8, 9 and 10, the top panel corresponds to early-stage sepsis, the bottom panel corresponds to late-stage sepsis, and the centre panel corresponds to an intermediate stage. As sepsis progresses, the attractor shrinks dramatically and peaks begin to appear in the scalar measure plots.

Accordingly, in one embodiment of the present invention, sepsis is diagnosed by comparing the attractor constructed from blood pressure data for an individual to a representative 'healthy' attractor. Sepsis/early shock is diagnosed if the size difference between the current attractor and the 'healthy' attractor exceeds a predefined threshold. In another embodiment, peaks are searched for in plots of one or more scalar measures derived from the attractor over time, and sepsis/early shock is diagnosed in response to a threshold number of peaks of a certain sharpness being found.

Figure 12:
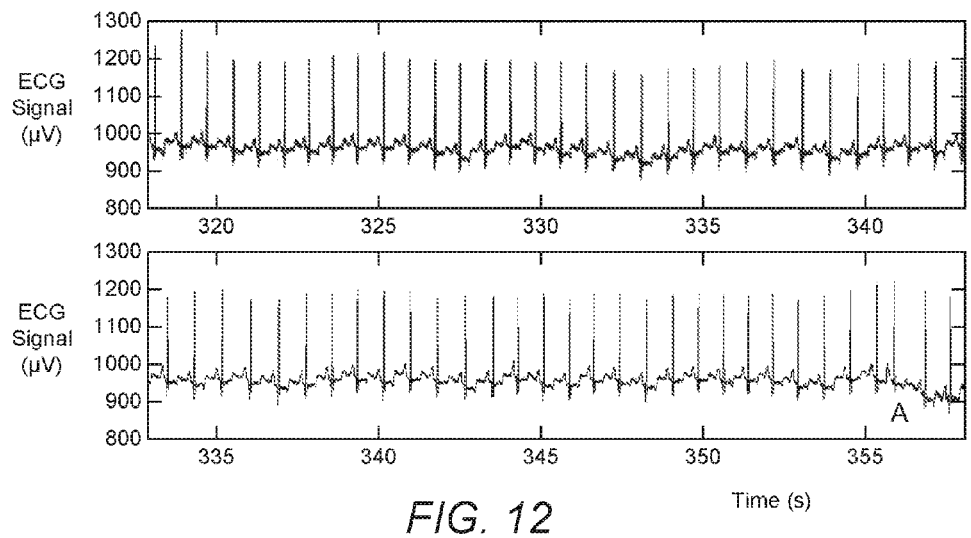
FIG. 12 illustrates human ECG data showing a healthy trace and a trace containing an arrhythmia.
Figure 13:
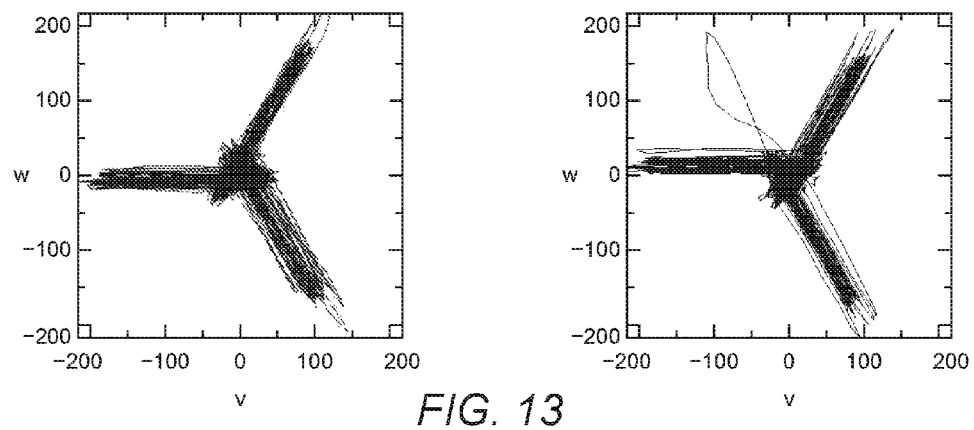
FIG. 13 illustrates attractors derived from the human ECG data shown in FIG. 12.

In an embodiment of the invention described above, sepsis/early shock is diagnosed based on characteristics of an attractor derived from blood pressure data. However, embodiments of the present invention are not limited to diagnosing sepsis/shock. An example of diagnosing another physiological condition, in this case arrhythmia, will now be described with reference to FIGS. 12 to 14. In FIG. 12, the top panel illustrates normal human ECG data, and the bottom panel illustrates human ECG data including an arrhythmia at the point marked 'A', around t=356 seconds. In FIG. 13, the left-hand panel illustrates an attractor derived from the normal human ECG data shown in FIG. 12, and the right-hand panel illustrates an attractor derived from the human ECG data including an arrhythmia from FIG. 12. As shown in FIG. 13, the arrhythmia event is clearly visible as a deviation from the regular 3-fold symmetry of the attractor.

Figure 14:
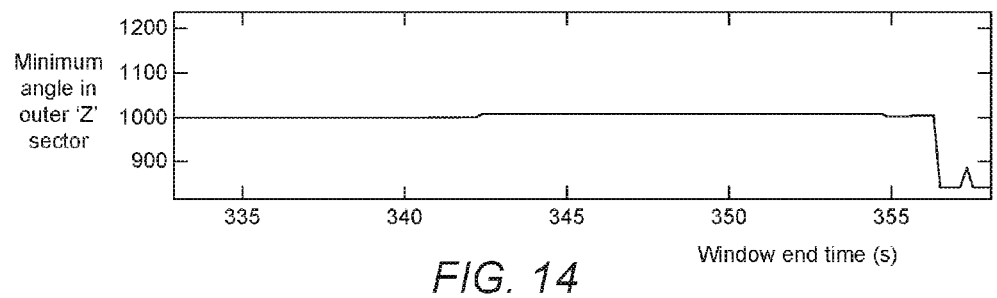
FIG. 14 illustrates a scalar measure derived from the attractor shown in FIG. 13, showing a sudden drop when the arrhythmia is detected.

A scalar measure derived from the right-hand attractor of FIG. 13 is illustrated in FIG. 14. In this embodiment, the scalar measure is the minimum angle in outer 'Z' sector. The arrhythmia event is clearly visible in a plot of the scalar measure as a reduction in the minimum angle in outer 'Z' sector at the window end time t=356 s.

Figure 15:
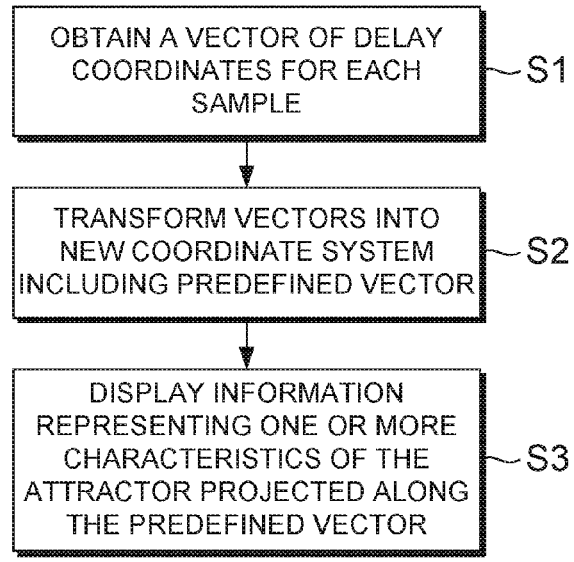
FIG. 15 illustrates a method of analysing periodic data, according to an embodiment of the present invention.

Referring now to FIG. 15, a method of analysing physiological data is illustrated, according to an embodiment of the present invention. First, in step S1 a vector of delay coordinates is obtained for each one of a plurality of samples of the physiological data in a time window. As described above, any number can be used for the embedding dimension of the vectors of delay coordinates, and various approaches are possible for determining a time delay to be used.

Then, in step S2 the obtained vectors are transformed into a coordinate system comprising a plurality of predefined vectors, to obtain a projection of an attractor of the physiological data along one of the predefined vectors. Examples of the present invention have been described above in which the predefined vector is x=y=z, but in other embodiments a different vector may be used. For example, in some embodiments it may be desirable to choose a predefined vector at a slight angle to the axis x=y=z, so that the attractor retains some information about vertical movement in the data, but is still predominately governed by the shape of the waveform between peaks.

Then, in step S3 information representing one or more characteristics of the obtained attractor is displayed, in order to enable a diagnosis. Various examples of types of information that can be displayed have been described above.

Figure 16:
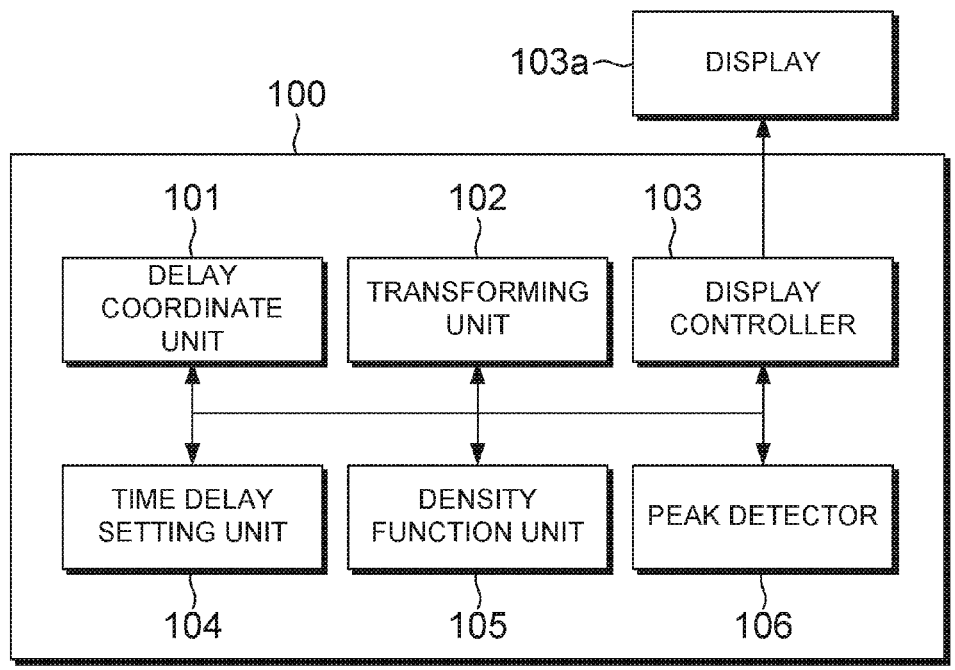
FIG. 16 illustrates a system for analysing periodic data, according to an embodiment of the present invention.

Referring now to FIG. 16, apparatus for analysing periodic physiological data is illustrated, according to an embodiment of the present invention. The various elements of the apparatus 100 can be implemented using hardware, software, or a combination of both. In software-implemented embodiments, one or more elements can be implemented as software instructions in one or more computer programs stored on a non-transitory computer-readable storage medium. When executed on one or more processors, the software instructions cause the relevant steps of the above-described methods to be performed.

The apparatus 100 comprises a delay coordinate unit 101, a transforming unit 102, and a display controller 103. The delay coordinate unit 101 is configured to obtain a vector of delay coordinates for each one of a plurality of samples of the physiological data in a time window. The transforming unit 102 is configured to transform each of the vectors into a coordinate system comprising a plurality of predefined vectors, to obtain a projection of an attractor of the physiological data along one of the predefined vectors. The display controller 103 is configured to display information representing one or more characteristics of the obtained attractor on a display 103a. The information representing one or more characteristics of the attractor can include an indicator of the repeat period T of a periodic waveform in the periodic data, which can be determined by the delay coordinate unit 101.

The display 103a can be included in the same physical device as other elements in the apparatus 100, or can be physically separate. Also, elements within the apparatus 100 of FIG. 16 can be embodied in the same physical device or can be distributed over different devices that are able to communicate with one another, for example over wired or wireless network connections.

Also, as shown in FIG. 16 the apparatus 100 further comprises a time delay setting unit 104 configured to determine a repeat period T of a periodic waveform in the physiological data, and select a value for a time delay τ based on the determined repeat period. In some embodiments, the repeat period T, or associated values, such as heart rate (HR) and heart rate variability (HRV) may be derived or displayed. The delay coordinate unit 101 is configured to obtain the vectors of delay coordinates based on the value of the time delay τ selected by the time delay setting unit 104. However, as described above, other approaches are possible for determining the time delay to be used, and so in some embodiments the time delay setting unit 104 can be omitted.

The apparatus of FIG. 16 further comprises a function generating unit 105 configured to determine a function relating to one or more of a density, shape, orientation, symmetry and size of the attractor projected along the predefined vector, and determine a value of a predefined quantity from the function. This value can then be displayed using the display controller 103, for example by displaying a plot of the predefined quantity as shown in FIG. 6 or 9. In other embodiments, the quantity may not be derived or displayed, and accordingly the function generating unit 105 can be omitted.

In some embodiments, the delay coordinate unit and the transforming unit are further configured to obtain a plurality of attractors by moving the time window through the data, and the function generating unit is further configured to determine a new function and a new value of the predefined quantity for each of the obtained attractors. The display controller can then display an animation of the attractors and/or the functions, and/or by plot a time trace of the predefined quantity against time.

In the present embodiment the apparatus further comprises a peak detector 106 configured to search for one or more peaks in the time trace the predefined quantity. In response to one or more peaks being found, the display controller 106 is configured to display information relating to the one or more peaks, for example by displaying indicators showing the positions of the detected peaks, as illustrated in FIG. 9. As described above, the presence of peaks can be useful in making a diagnosis. However, in some embodiments the peak detector can be omitted, for example, when it is only desired to display a visual representation of the attractor as shown in FIG. 9.

Embodiments of the invention can be used to provide information of diagnostic value in a preclinical or clinical environment, including characterisation of both the healthy and pathophysiological state. Also, although embodiments of the present invention have been described in which an attractor is constructed in three dimensions, and then projected onto a plane orthogonal to a chosen axis to give a two-dimensional projection, the invention is not limited to this number of dimensions. In other embodiments, any number of dimensions greater than or equal to two can be used for the delay coordinate vectors. For example, to extend the delay coordinate vectors described above to n dimensions, new variables $x_i$ can be defined as follows:

$$x_i = x(t-(i-1)\tau)$$

where i=1, . . . , n. The central axis can then be defined as the axis $$x_1 = x_2 = \ldots = x_n$$

and additional vectors $v_n$ orthogonal to the central axis can be defined as necessary. For example, additional mutually orthogonal vectors can be defined as follows:

$$v_1 = (1, \ldots, 1)^T$$

$$v_2 = (1, -1, 0, \ldots, 0)^T$$

$$v_3 = (1, 1, -2, 0, \ldots, 0)^T$$

$$v_n = (1, \ldots, 1, -(n-1))^T$$

Coordinates of the vectors $v_2, \ldots v_n$ give a projection along the central axis in this case.

Embodiments of the invention have been described in which physiological data is analysed using a delay coordinates method, to enable diagnosis of certain physiological conditions that would not normally be possible by simply viewing a trace of the physiological data against time. However, the present invention is not limited to analysing physiological data. In other embodiments a different type of periodic data may be analysed, such as engineering data. An example of delay coordinate analysis applied to periodic engineering data will now be described with reference to FIGS. 17 and 18, according to an embodiment of the present invention.

FIG. 17 illustrates bending moment data from a wind turbine, FIG. 18 illustrates an attractor derived from the bending moment data shown in FIG. 17, and FIG. 19 is a density plot for the attractor shown in FIG. 18. The periodic data shown in FIG. 17 comprises 5 minutes of bending moment data from the mudline (sea bed) of an offshore wind turbine, measured at 40 Hertz. The bending moment data is influenced by multiple dynamic loads, including wind, waves, the blade rotational frequency and the blade passing frequency. As a result, the bending moment data is a complex, noisy signal that cannot easily be interpreted in a conventional time plot as shown in FIG. 17. However, fatigue damage can be more easily detected by plotting an attractor as shown in FIG. 17, as a deviation from the normal attractor form, which in this example is approximately circular. For example, fatigue may be detected as a result of changes in the form of the density of the attractor as plotted in FIG. 19.

Whilst certain embodiments of the invention have been described herein with reference to the drawings, it will be understood that many variations and modifications will be possible without departing from the scope of the invention as defined in the accompanying claims.

The invention claimed is:

1. A method of analysing periodic data, the method comprising:
    obtaining a vector of delay coordinates for each one of a plurality of samples of the periodic data in a time window;
    transforming each of the vectors into a coordinate system comprising a plurality of predefined vectors, to obtain a projection of an attractor of the periodic data along one of the predefined vectors; and
    displaying information representing one or more characteristics of the obtained attractor.

2. The method of claim 1, further comprising:
    determining a repeat period T of a periodic waveform in the periodic data; and
    selecting a value for a time delay $\tau$ based on the determined repeat period,
    wherein the vectors of delay coordinates are obtained based on the selected value of the time delay $\tau$.

3. The method of claim 1, wherein the information representing one or more characteristics of the obtained attractor includes a visual representation of the attractor projected along said predefined vector, and/or includes an indicator of the repeat period T of a periodic waveform in the periodic data.

4. The method of claim 1, wherein the information representing one or more characteristics of the obtained attractor includes the value of a predefined quantity relating to the attractor, and further comprising:
    determining a function relating to one or more of a density, shape, orientation, symmetry and size of the attractor projected along said predefined vector; and
    determining the value of the predefined quantity from the function.

5. The method of claim 4, further comprising:
    obtaining a plurality of attractors by moving the time window through the periodic data; and
    determining a new function relating to one or more of a density, shape, orientation, symmetry and size of the attractor and a new value of the predefined quantity for each of the obtained attractors,
    wherein displaying the information representing one or more characteristics of the attractor comprises displaying an animation of the attractors and/or the function, and/or comprises plotting a time trace of the predefined quantity against time.

6. The method of claim 1, wherein the periodic data is physiological data and the method further comprises:
    diagnosing disease or deviation from baseline in a subject suspected of suffering from disease based on the information representing one or more characteristics of the obtained attractor.

7. The method of claim 6, wherein the disease being diagnosed is sepsis/shock or a sepsis/shock-related disease, a disease associated with an abnormal rhythm of the heart or a disease associated with a disorder of the contractility of the heart or disorder of the vascular network.

8. A non-transitory computer-readable storage medium arranged to store software instructions which, when executed on one or more processors, perform the method of claim 1.

9. A method for diagnosing disease or deviation from baseline in a subject, the method comprising:
    obtaining a vector of delay coordinates for each one of a plurality of samples of physiological data in a time window;
    transforming each of the vectors into a coordinate system comprising a plurality of predefined vectors, to obtain a projection of an attractor of the physiological data along one of the predefined vectors; and
    displaying information representing one or more characteristics of the obtained attractor,
    wherein a change in said one or more characteristics of the attractor, relative to the corresponding parameter for a subject not suffering from a disease, indicates that the subject is suffering from a disease.

10. The method of claim 9, wherein the disease being diagnosed is sepsis/shock or a sepsis/shock-related disease, a disease associated with an abnormal rhythm of the heart or a disease associated with a disorder of the contractility of the heart or disorder of the vascular network.

11. Apparatus for analysing periodic data, the apparatus comprising:
    a delay coordinate unit configured to obtain a vector of delay coordinates for each one of a plurality of samples of the periodic data in a time window;
    a transforming unit configured to transform each of the vectors into a coordinate system comprising a plurality of predefined vectors, to obtain a projection of an attractor of the periodic data along one of the predefined vectors; and
    a display controller configured to display information representing one or more characteristics of the obtained attractor on a display.

12. The apparatus of claim 11, further comprising:
    a time delay setting unit configured to determine a repeat period T of a periodic waveform in the periodic data, and select a value for a time delay $\tau$ based on the determined repeat period,
    wherein the delay coordinate unit is configured to obtain the vectors of delay coordinates based on the value of the time delay $\tau$ selected by the time delay setting unit.

13. The apparatus of claim 11, wherein the information representing one or more characteristics of the obtained attractor includes a visual representation of the attractor projected along said predefined vector, and/or includes an indicator of the repeat period T of a periodic waveform in the periodic data.

14. The apparatus of claim 11, wherein the information representing one or more characteristics of the obtained attractor includes the value of a predefined quantity relating to the attractor.

15. The apparatus of claim 14, further comprising:
a function generating unit configured to determine a function relating to one or more of a density, shape, orientation, symmetry and size of the attractor projected along said predefined vector, and determine the value of the predefined quantity from the function.

16. The apparatus of claim 15, wherein the delay coordinate unit and the transforming unit are further configured to obtain a plurality of attractors by moving the time window through the periodic data, and the function generating unit is further configured to determine a new function relating to one or more of a density, shape, orientation, symmetry and size of the attractor and a new value of the predefined quantity for each of the obtained attractors, and
wherein the display controller is configured to display the information representing one or more characteristics of the attractor by displaying an animation of the attractors and/or the function, and/or by plotting a time trace of the predefined quantity against time.

17. The apparatus of claim 16, further comprising:
a peak detector configured to search for one or more peaks in the time trace of the predefined quantity,
wherein in response to one or more peaks being found, the display controller is configured to display information relating to the one or more peaks.

18. The apparatus of claim 15, wherein the predefined quantity relates to a width, density, shape, or size of a band in the projection of the attractor along said predefined vector, or the orientation, symmetry or size of the attractor in the projection of the attractor along said predefined vector.

19. The apparatus of claim 18, further comprising:
a searching unit configured to search for an irregular event in the periodic data, based on the predefined quantity relating to the width of the band in the projection of the attractor along said predefined vector.

20. The apparatus of claim 11, wherein the obtained vectors of delay coordinates are three-dimensional vectors [x, y, z], and said predefined vector is parallel to the axis x=y=z.

\* \* \* \* \*

UNITED STATES PATENT AND TRADEMARK OFFICE
CERTIFICATE OF CORRECTION

PATENT NO. : 9,940,741 B2  
APPLICATION NO. : 15/118405  
DATED : April 10, 2018  
INVENTOR(S) : Philip Aston Page 1 of 1

It is certified that error appears in the above-identified patent and that said Letters Patent is hereby corrected as shown below:

On the Title Page

In Column 1, item (65) at Line 2, Below "US 2017/0132816 A1 May 11, 2017" insert --Foreign Application Priority Data Feb. 14, 2014 (GB) 1402680.1--, as new item.

In the Specification

In Column 6 at Line 25, Change "10" to --11F--.

Signed and Sealed this  
Thirty-first Day of July, 2018

Andrei Iancu  
*Director of the United States Patent and Trademark Office*